United States Patent [19]

Neuzil

[11] 3,997,620

[45] Dec. 14, 1976

[54] PROCESS FOR SEPARATING PARA-XYLENE

[75] Inventor: Richard W. Neuzil, Downers Grove, Ill.

[73] Assignee: UOP Inc., Des Plaines, Ill.

[22] Filed: Oct. 28, 1975

[21] Appl. No.: 626,152

[52] U.S. Cl. .................. 260/674 SA; 208/310 Z
[51] Int. Cl.$^2$ .......................................... C07C 7/13
[58] Field of Search ........... 260/674 SA; 208/310 Z

[56] References Cited

UNITED STATES PATENTS

| | | | |
|---|---|---|---|
| 3,686,342 | 8/1972 | Neuzil | 260/674 SA |
| 3,696,107 | 10/1972 | Neuzil | 260/674 SA |
| 3,707,550 | 12/1972 | Stine et al. | 260/674 SA |
| 3,715,409 | 2/1973 | Broughton | 260/674 SA |
| 3,734,974 | 5/1973 | Neuzil | 260/674 SA |

*Primary Examiner*—Delbert E. Gantz
*Assistant Examiner*—C. E. Spresser
*Attorney, Agent, or Firm*—James R. Hoatson, Jr.; Thomas K. McBride; William H. Page, II

[57] ABSTRACT

A process for separating para-xylene in high purity and at high recovery from a feed stream comprising para-xylene and at least one other $C_8$ aromatic isomer which employs an adsorbent comprising a type X or a type Y zeolite containing barium and strontium at the exchangeable cationic sites in a weight ratio of barium to strontium of from about 1:1 to about 15:1 to selectively adsorb para-xylene from the feed stream and a desorbent material comprising para-diethylbenzene to remove the adsorbed para-xylene from the adsorbent.

20 Claims, No Drawings

PROCESS FOR SEPARATING PARA-XYLENE

BACKGROUND OF THE INVENTION

1. Field of the Invention

The field of art to which this invention pertains is hydrocarbon separation. More specifically the invention relates to an improved process for the separation of para-xylene from a feed stream comprising para-xylene and at least one other $C_8$ aromatic isomer which process employs a particular solid adsorbent and a particular desorbent material to effect the selective adsorption and desorption of para-xylene.

2. Description of the Prior Art

The prior art has recognized that type X or type Y zeolites containing selected cations at the exchangeable cationic sites can be used to separate para-xylene from a feed mixture containing para-xylene and at least one other $C_8$ aromatic isomer.

In my U.S. Pat. Nos. 3,558,730 and 3,663,638 for instance, I recognized the particular suitability of a crystalline aluminosilicate adsorbent containing both barium and potassium at the exchangeable cationic sites for use in a para-xylene separation process. My U.S. Pat. No. 3,734,974 discloses the particular effectiveness of an adsorbent comprising type X or type Y zeolites containing barium cations at the exchangeable cationic sites and water within the zeolite when used in a process for separating para-xylene.

I have also previously discovered the suitability of particular materials for use as desorbent materials in $C_8$ aromatic adsorptive separation processes. In my U.S. Pat. No. 3,558,732 I discovered an improved process for separating at least one $C_8$ aromatic isomer from a feed containing a mixture of $C_8$ aromatic hydrocarbons wherein the improvement was employing a desorbent material containing toluene. A desorbent material containing toluene is particularly well suited for use in a process which separates para-xylene from an extracted feed stream, that is, one containing essentially no $C_8$ non-aromatics. With such a desorbent material and with extracted feed streams separation of para-xylene in both high purity (greater than about 99%, expressed as a percent of $C_8$ aromatics present) and high yields (greater than about 98%) is common. In my U.S. Pat. No. 3,686,342 I discoverd an improved process for separating para-xylene from a feed containing a mixture of $C_8$ aromatics wherein the improvement was employing a desorbent material containing paradiethylbenzene. While this desorbent material can be used with extracted feed streams, it is particularly useful in separating para-xylene from non-extracted feed streams, that is, those containing $C_8$ non-aromatics in varying concentrations. When a toluene desorbent is used with a nonextracted feed stream $C_8$ non-aromatics, such as napthenes, which have a boiling point close to that of toluene, make clean separation and recovery of the toluene desorbent material from the extract and raffinate output streams difficult if not impossible resulting in eventual contamination of the toluene desorbent. Thus the use of a desorbent material comprising para-diethylbenzene extends the separation process to a wider variety of feed stocks, such as non-extracted $C_8$ aromatic fractions. Being able to use non-extracted $C_8$ aromatic fractions as feed streams to the para-xylene separation process eliminates the need for the aromatic extraction processing step otherwise required in the preparation of a feed stream to be used in a process employing toluene as a desorbent material.

I have discovered, however, that when a desorbent material containing para-diethylbenzene is used with certain adsorbents, for example those comprising type X or type Y zeolites containing barium and potassium at the exchangeable cationic sites, that the selectivity of the adsorbent is higher for the desorbent material than it is for para-xylene. This results in the inability of the para-xylene separation process employing this adsorbent and a desorbent material containing paradiethylbenzene to obtain yields of high purity (greater than about 99% expressed as a percent of the $C_8$ aromatics present) para-xylene of greater than about 95%. Thus although about the same para-xylene purities can be obtained as those obtainable from a separation process using toluene as a desorbent material, the para-xylene yields are not as high as those from the separation process using toluene.

I have further discovered that when an adsorbent comprising type X or type Y zeolite containing barium and strontium at the exchangeable cationic sites is used in the para-xylene separation process with a desorbent material containing para-diethylbenzene that the problem is eliminated. Thus the process of my invention makes separation of paraxylene in both high purity (greater than about 99%) and high yields (greater than about 95%) possible. Para-xylene is a valuable raw material used to make polyester fibers, polyester films and polyethylene terephthalate and polybutylene terephthalate resins.

SUMMARY OF THE INVENTION

It is, accordingly, a broad objective of my invention to provide a process for the separation of high purity para-xylene at high recoveries from a feed mixture containing para-xylene and at least one other $C_8$ aromatic. It is a more specific objective of my invention to provide a process for separating high purity para-xylene at high recoveries by adsorption of para-xylene on a particular adsorbent from a feed mixture containing para-xylene, at least one other $C_8$ aromatic, and $C_8$ non-aromatics followed by desorption with a desorbent material containing paradiethylbenzene.

In brief summary my invention is in one embodiment a process for separating para-xylene from a feed stream containing para-xylene and at least one other $C_8$ aromatic isomer which process comprises the steps of (a) contacting the feed stream with an adsorbent comprising type X or type Y zeolite containing barium and strontium at the exchangeable cationic sites in a weight ratio of barium to strontium of from about 1:1 to about 15:1 to effect the selective adsorption of para-xylene; (b) removing a raffinate component comprising a less selectively adsorbed $C_8$ aromatic from said adsorbent; (c) contacting said adsorbent with a desorbent material comprising para-diethylbenzene at desorption conditions to effect the desorption of para-xylene from said adsorbent; and, (d) removing from said adsorbent an extract component comprising para-xylene.

In another embodiment my invention is a process for the separation of para-xylene from a feed stream comprising para-xylene and at least one other $C_8$ aromatic isomer which process employs an adsorbent comprising type X or type Y zeolite containing barium and strontium at the exchangeable cationic sites in a weight ration of barium to strontium of from about 1:1 to about 15;1 and which process compises the steps of:

(a) maintaining net fluid flow through a column of an adsorbent in a single direction, which column contains at least three zones having separate operational functions occurring therein and being serially interconnected with the terminal zones of the column connected to provide a continuous connection of said zones; (b) maintaining an adsorption zone in said column, said zone defined by the adsorbent located between a feed input stream at an upstream boundary of said zone and a raffinate output stream at a downstream boundary of said zone; (c) maintaining a purification zone immediately upstream from said adsorption zone, said purification zone defined by the adsorbent located between an extract output stream at an upstream boundary of said purification zone and the feed input stream at a downstream boundary of said purification zone; (d) maintaining a desorption zone immediately upstream from said purification zone, said desorption zone defined by the adsorbent located between a desorbent input stream at an upstream boundary of said zone and the extract output stream at a downstream boundary of said zone; (e) passing the feed stream into the adsorption zone at adsorption conditions to effect the selective adsorption of para-xylene by the adsorbent in the adsorption zone and withdrawing a raffinate output stream from the adsorption zone; (f) passing a desorbent material comprising para-diethylbenzene into the desorption zone at desorption conditions to effect the displacement of para-xylene from the adsorbent in the desorption zone; (g) withdrawing an extract stream comprising para-xylene and desorbent material from the desorption zone; (h) passing at least a portion of said extract output stream to a separation means and therein separating at separation conditions desorbent material to produce a para-xylene product substantially free of desorbent material; and (i) periodically advancing through the column of adsorbent in a downstream direction with respect to fluid flow in the adsorption zone the feed input stream, raffinate output stream, desorbent input stream, and extract output stream to effect the shifting of zones through the adsorbent and the production of extract output and raffinate output streams, wherein the improvement comprises employing an adsorbent comprising type X or type Y zeolite containing both barium and strontium at the exchangeable cationic sites.

Other objects and embodiments of the present invention encompass details about feed mixtures, adsorbents, desorbent materials and operating conditions all of which are hereinafter disclosed in the following discussion of each of the facets of the present invention.

DESCRIPTION OF THE INVENTION

In order to gain a better understanding of the process of this invention, the following definitions of terms that are used throughout this specification are given.

The term "feed stream" indicates a stream in the process through which feed material passes to the adsorbent. A feed material comprises one or more extract components and one or more raffinate components.

An "extract component" is a compound or type of compound that is more selectively adsorbed by the adsorbent while a "raffinate component" is a compound or type of compound that is less selectively adsorbed. In this process, para-xylene is the extract component and another xylene isomer or ethylbenzene is a raffinate component. The term "raffinate stream" or "raffinate output stream" means a stream through which most of the raffinate components are removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high purity para-xylene at high recoveries, it will be appreciated that an extract component is never completely adsorbed by the adsorbent, nor is a raffinate component completely non-adsorbed by the adsorbent, Therefore, small amounts of a raffinate component can appear in the extract stream and, likewise, small amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of para-xylene to that of a less selectively adsorbed $C_8$ aromatic isomer such as ethylbenzene will be lowest in the raffinate stream, next highest in the feed mixture, and the highest in the extract stream. Likewise, the ratio of the concentration of a less selectively adsorbed $C_8$ aromatic such as ethylbenzene to that of the more selectively adsorbed para-xylene will be highest in the raffinate stream, next highest in the feed mixture, and the lowest in the extract stream.

The term "desorbent material" shall mean generally a material capable of desorbing an extract component. The term "desorbent stream" or "desorbent input stream" indicates the stream through which desorbent material passes to the adsorbent.

The term "selective pore volume" of the adsorbent is defined as the volume of the adsorbent which selectively adsorbs extract components from the feed stock. The term "non-selective void volume" of the adsorbent is the volume of the adsorbent which does not selectively retain extract components from the feed stock. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components.

The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise para-xylene and at least one other $C_8$ aromatic isomer. Mixtures containing substantial quantites of para-xylene and other $C_8$ aromatic isomers generally are produced by reforming and isomerization processes, processes which are well known to the refining and petrochemical arts.

In reforming processes, a naphtha feed is contacted with a paltinum-halogen-containing catalyst at severities selected to produce an effluent containing $C_8$ aromatic isomers. Generally the reformate is then fractionated to concentrate the $C_8$ aromatic isomers in a $C_8$ fraction which will contain the $C_8$ aromatic isomers as well as $C_8$ non-aromatics.

Xylene isomerization processes isomerize at isomerization conditions a xylene mixture which is deficient in one or more isomers to produce an effluent containing approximately equilibrium quantities of the $C_8$ aromatic isomers as well as $C_8$ non-aromatics. The equilibrium compositions of the xylene isomers and ethylbenzene at various temperatures are shown in Table 1 below.

Table 1

| Equilibrium $C_8$ Aromatic Compositions* | | | |
|---|---|---|---|
| Temperature, ° C. | 327 | 427 | 527 |
| Mole percent of $C_8$ aromatic isomers | | | |
| Ethylbenzene | 6 | 8 | 11 |
| Para-xylene | 22 | 22 | 21 |
| Meta-xylene | 50 | 48 | 45 |
| Ortho-xylene | 22 | 22 | 23 |

*Base on API sources

Para-xylene is separated from feedstreams which are, generally speaking, either extracted or non-extracted. An extracted feedstream is an extract product stream which has been produced by a typical solvent extraction process from a feed mixture containing both $C_8$ aromatic isomers and $c_8$ non-aromatics. The particular solvent selectively extracts the $C_8$ aromatics and an extract product essentially free of non-aromatics is produced. Non-extracted feedstreams are those containing both $C_8$ aromatic isomers and $C_8$ non-aromatics. Typically they are isomerates or $C_8$ fractions prepared by fractionating hydrogenated pyrolysis naphthas or reformates. Shown in Table No. 2 is an analysis of a typical non-extracted reformate $C_8$ heartcut in which the total $C_8$ non-aromatics, paraffins and monocycloparaffins, are 26.5 wt. %.

Table No. 2

Typical Non-Extracted Reformate $C_8$ Heartcut Analysis

| M.S. Hydrocarbon Breakdown, wt. % | |
|---|---|
| Aromatics | |
| $C_8$ | 73.2 |
| $C_9$ | 0.3 |
| | 73.5 |
| Paraffins | |
| $C_6$ | 0.1 |
| $C_7$ | 0.2 |
| $C_8$ | 2.1 |
| $C_9$ | 20.7 |
| $C_{10}$ | 0.8 |
| | 23.9 |
| Monocycloparaffins | |
| $C_6$ | 1.0 |
| $C_7$ | 1.2 |
| $C_8$ | 0.2 |
| $C_9$ | 0.2 |
| | 2.6 |

Likewise the effluent from a catalytic xylene isomerization process also contains varying amounts of these $C_8$ non-aromatics. Table No. 3 shows the amounts of individual $C_8$ non-aromatics contained in a typical isomerate and their respective normal boiling points. Here the total $C_8$ non-aromatics amount to 8.52%.

Table No. 3

Individual $C_8$ Non-Aromatic Components in a Typical Xylene Isomerization Reactor Effluent and Their Normal Boiling Points

| $C_8$ Paraffins | Wt. % In Reactor Effluent | Normal Boiling Point, ° F. |
|---|---|---|
| 2,4-dimethylhexane | 0.33 | 229.0 |
| 2,3-dimethylhexane | 0.33 | 240.1 |
| 2-methylheptane | 0.63 | 243.8 |
| 4-methylheptane | 0.90 | 243.9 |
| n-octane | 0.33 | 258.2 |
| | 2.52 | |
| $C_8$ Naphthenes | | |
| 1,1,3-trimethylcyclopentane | 0.42 | 220.8 |
| 1,trans-2,cis-4-trimethylcyclopentane | .48 | 228.7 |
| 1,trans-2,cis-3-trimethylcyclopentane | .12 | 230.4 |
| 1,1,2-trimethylcyclopentane | .18 | 236.7 |
| 1,cis-2,trans-4-trimethylcyclopentane | .12 | 242.1 |
| 1,cis-2,trans-3-trimethylcyclopentane | .12 | 243.5 |
| 1,1-dimethylcyclohexane | .36 | 247.2 |
| 1,trans-4-dimethylcyclohexane | .90 | 246.8 |
| 1,cis-3-dimethylcyclohexane | | 248.2 |
| 1-methyl,cis-3-ethylcyclopentane | .42 | 250.0 |
| 1-methyl,trans-3-ethylcyclopentane | 1.02 | 250.0 |
| 1-methyl,trans-2-ethylcyclopentane | | 250.2 |
| 1-methyl,4-ethylcyclopentane | | & — |
| 1,cis-2,cis-3-trimethylcyclopentane | .30 | 253.4 |
| 1,trans-2-dimethylcyclohexane | | 254.2 |
| 1,trans-3-dimethylcyclohexane | .42 | 256.0 |
| 1,cis-4-dimethylcyclohexane | | 255.8 |
| isopropylcyclopentane | .24 | 259.6 |
| 1-methyl,cis-2-ethylcyclopentane | .12 | 262.5 |
| 1,cis-2-dimethylcyclohexane | .12 | 265.5 |
| ethylcyclohexane | .66 | 269.2 |

Table No. 3-continued

Individual $C_8$ Non-Aromatic Components in a Typical Xylene Isomerization Reactor Effluent and Their Normal Boiling Points

| | 6.00 | |
|---|---|---|
| Aromatics | | |
| toluene | — | 231.1 |
| ethylbenzene | — | 277.1 |
| p-xylene | — | 281.0 |
| m-xylene | — | 282.4 |
| o-xylene | — | 291.9 |

At least a portion of the extract output stream and preferably at least a portion of the raffinate stream from the para-xylene separation process are passed to separation means, typically fractionators, where desorbent material is separated to produce an extract product (paraxylene) and a raffinate product. With extracted feedstreams the separation of toluene desorbent from the extract output stream and from the raffinate output stream is easily accomplished because of the 40° to 50° F. difference in their boiling points as shown in Table No. 3.Typically the raffinate output stream fractionator is operated such that a small amount of desorbent is left in the bottoms product to prevent accumulation of contaminant $C_8$ aromatics in the circulating desorbent. Desorbent material in the bottoms or extract product of the extract output stream fractionator however would reduce the purity of the para-xylene product. Therefore, a sharp separation leaving little or no desorbent in the bottoms product is desired.

With non-extracted feedstreams the presence of $C_8$ non-aromatics makes the separation of toluene desorbent material more difficult which can result in accumulation of $C_8$ non-aromatics in the circulating desorbent and contamination of the para-xylene product. With such feedstreams, desorbent materials containing para-diethylbenzene are therefore preferred.

Feedstreams to out process can also comprise effluent streams from processes which have removed varying amounts of one or more $C_8$ aromatic isomers. As one example, at least a protion of the ortho-xylene may have been previously removed by fractionation from a feed mixture containing the $C_8$ aromatic isomers. Ortho-xylene has a boiling point of about 5° F. higher than that of the nearest other $C_8$ aromatic (meta-xylene) and hence can be removed as a bottoms product from ortho-xylene fractionator towers. Such towers will typically contain about 100 to 105 actual trays and will operate with about a 5–8 to 1 reflux to feed ratio. The concentration of ortho-xylene in the effluent or overhead from this fractionation process which can be used as a feedstream to our process may then be less than the concentrations of any other xylene isomer or ethylbenzene. Alternatively or additionally at least a portion of the ethylbenzene may have been previously removed from the xylene isomers by fractionation. Because the boiling point of ethylbenzene is within about 4° F. of that of para-xylene, however, the fractionation can be achieved only with the more intricate super-fractionators. Typical ethylbenzene fractionators contain 300 to 400 actual trays and require about a 25–50 to 1 reflux to feed ratio. As another example, a portion of the para-xylene may have been previously removed from a $C_8$ aromatic feed mixture by a fractional crystallization process. In this situation, the concentration of para-xylene in the process effluent may be less than the concentration of any other xylene isomer or ethylbenzene.

Desorbent materials used in various adsorptive separation processes vary depending upon such factors as the type of operation employed. In the swing-bed system in which the selectively adsorbed feed component is removed from the adsorbent by a purge stream desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated at substantially constant pressures and temperatures to insure liquid phase, the desorbent material relied upon must be judiciously selected to satisfy, hopefully, all of several criteria. First, the desorbent material should displace the extract components from the adsorbent with resonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials should additionally be substances which are easily separable from the feed mixture that is passed into the process. Both the raffinate stream and the extract stream are removed from the adsorbent in admixture with desorbent material and without a method of separating desorbent material, such as distillation, the purity of the extract components and the raffinate component would not be very high, nor would the desorbent material be available for reuse in the process. It is therefore contemplated that any desorbent material will have an average boiling point different than that of the feed mixture to permit separation therefrom by distillation. The boiling range of the desorbent material may be higher or lower than that of the feed mixture.

The prior art has recognized that desorbent materials comprising certain aromatic hydrocarbons such as toluene and para-diethylbenzene most closely meet these criteria and are particularly effective. This process is primarily concerned with desorbent materials comprising para-diethylbenzene which are used particularly when the feed stream to the separation process contains $C_8$ non-aromatics. It is preferable that this desorbent material contain only para-diethylbenzene and no other diethylbenzene isomer. Typical concentrations of para-diethylbenzene when paradiethylbenzene is the sole diethylbenzene isomer present in the desorbent material can range from a few volume percent up to about 100 volume percent. More preferably when no other diethylbenzene isomer is present the para-diethylbenzene concentration will be from about 50 to about 75 vol. % of the desorbent material. Desorbent materials can also comprise mixed diethylbenzenes, one of which will be para-diethylbenzene. Typically a diethylbenzene mixture will contain roughly about 60 vol. % meta-diethylbenzene, 7 vol. % ortho-diethylbenzene, and 26 vol. % para-diethylbenzene along with approximately 7 vol. % of butylbenzenes. Mixtures comprising para-diethylbenzene and diluents are also effective as desorbent materials. Such diluents must be compatible with the adsorbent and feed mixture as described above and must be easily separable from the feed mixture. Diluents which can be used include materials such as saturated hydrocarbons, including the paraffinic type hydrocarbons and cycloparaffins, and additionally the carbocyclic ring compounds. Typically, the diluent materials from the saturated paraffin group consist of the straight or branched chain paraffins having from about 4 to about 20 carbon atoms per molecule and preferably having from about 5 to about 15 carbon atoms per molecule. Cycloparaffins can include the cyclohexane, cyclopentanes, and branched derivatives thereof. Additional carbocyclic ring compounds including Decalin and Decalin derivatives containing branched chains can be utilized and are preferred as one diluent to be used successful the process of this invention.

It has also been recognized that certain characteristics of adsorbents are highly desirable, if not absolutely necessary, to the sucessful operation of a selective adsorption process. Among such characteristics are: adsorptive capacity for some volume of an extract component per volume of adsorbent; the selective adsorption of extract components with respect to a raffinate component and the desorbent material; and sufficiently fast rates of adsorption and desorption of the extract components to and from the adsorbent.

Capacity of the adsorbent for adsorbing a sepecific volume of one or more extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of he adsorbed phase over the ratio of the same two components in the unadsorbed phase at equilibrium conditions.

Relative selectivity is shown as Equation 1 below.

Equation 1

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed adsorbent did not change composition after contacting the bed of adsorbent. In other words, there was no net transfer of material occurring between the unadsorbed adn adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or less than 1 with respect to all extract components so that all of the extract components can be extracted as a class and all raffinate components clearly rejected into the raffinate stream. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber.

The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing desorbent deesorbent material through the adsorbent chamber. At a convenient time, a pulse of feed containing known concentrations of a non-adsorbed paraffinic tracer (n-nonane for instance) and of the particular $C_8$ aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, Calif., Mar. 28 through Apr. 2, 1971.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences betwen the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of specific $C_8$ aromatic isomers is dependent on differences in electrochemical atttaction of the different isomers and the adsorbent rather than on pure physical size differences in the isomer molecules.

In hydrated form, the crystalline aluminosilicates generally encompass those zeolites represented by the Formula 1 below:

Formula 1

$M_{2/n}O:Al_2O_3:wSiO_2:yH_2O$ where M is a cation which balances the electrovalence of the tetrahedra and is generally referred to as an exchangeable cationic site, $n$ represents the valence of the cation, $w$ represents the moles of $SiO_2$, and $y$ represents the moles of water. The cation M may be one or more of a number of possible cations.

The prior art has generally recognized that adsorbents comprising the type X and the type Y zeolites can be used in certain adsorptive separation processes. These zeolites are described and defined in U.S. Pat. Nos. 2,882,244 and 3,120,007 respectively. As the type X and type Y zeolites are initially prepared, the cation M is usually predominately sodium and the zeolites are therefore referred to as sodium-type X zeolite and sodium-type Y zeolite. Depending upon the purity of the reactants used to make the zeolites, other cations may be present as impurities.

Cations occupying exchangeabel cationic sites in the zeolite may be replaced with other cations by ion exchange methods generally well known to those having ordinary skill in the field of crystalline aluminosilicates. Such methods are generally performed by contacting the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeabel sites as impurities in a sodium-type X or sodium-type Y zeolite can be partially or essentially completely replaced with other cations.

Adsorbents which have been found to possess the characteristics described above and which are particularly suitable for use in a process for separating para-xylene which process employs a desorbent material containing para-diethylbenzene are those comprising type X or type Y zeolites containing barium and strontium cations at the exchangeable cationic sites. Such adsorbents will preferably have a weight ratio of barium to strontium within the range of from about 1:1 to about 15:1 and more preferably from about 5:1 to about 15:1. The adsorbents will be prepared by essentially completely ion-exchanging sodium-type X or sodium-type Y base materials with barium and strontium cations to produce the desired ratio. The term "essentially complete" shall mean that the residual sodium content of the adsorbent after the ion exchanges is less that about 2 wt. % $Na_2O$. A suitable base material which can be used to make adsorbents for this process is "Molecular Sieves 13X" commercially available from the Linde Company, Tonawanda, N.Y. Y.

Adsorbent water content has also been found to be necessary to maintain optimum adsorbent performance particularly, as disclosed in my U.S. Pat. No. 3,734,974, when the adsorbent has a high barium cation content. The preferred water content of the adsorbent used in this process will be from about 1.0 to about 5 wt. % water measured by loss on ignition at 500° C. This amount of water may be maintained if necessary by adding water to the adsorbent either on an intermittent or more preferably on a continuous basis by itself or in admixture with feed or desorbent material to maintain the desired concentrations of water on the adsorbent.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed exchangeable simulated moving-bed countercurrent flow sytems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589.

exchangeable In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, form the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a protion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 to zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instnace, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting condutis can be connected to transfer taps which during the normal operations do not function as a conduit through which material passes into or out of the process.

It is contemplated that at least a portion of the extract output stream will pass into a separation means wherein desorbent material can be separated to produce an extract product (para-xylene) substantially free of desorbent material. Preferably, but not necessary to the operation of the process, at least a portion of the raffinate output stream will also be passed to a separation means wherein desorbent material can be separated for reuse in the process and a raffinate product substantially free of desorbent material can be produced. The term "substantially free" shall mean that the concentration of desorbent material in either the extract product or the raffinate product shall be less than about 5 vol. % and more preferably less than about 1 vol. %. The separation means will typically be a fractionation column, the design and operation of which is well known to the separation art.

Reference can be made to D. B. Broughton U.S. Pat. No. 2,985,589, and to a paper entitled "Continuous Adsorptive Processing — A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of para-xylene product that can be obtained with liquid-phase operation over those obtained with vapor-phase operation. Adsorption conditions will include a temperature range of from 40° to about 250° C. and a pressure range of from about atmospheric to about 500 psig to insure liquid phase. Desorption conditions will include the same range of temperatures and pressures as used for adsorption conditions.

The size of the units which can utilize the process of this invention can vary anywhere from those of pilot-plant scale (see for example my assignee's U.S. Pat. No. 3,706,812) to those of commercial design and can range in flow rates from as little as a few cc. an hour up to many thousands of gallons per hour.

I have discovered that when certain adsorbents, for example those comprising type X or type Y zeolites containing barium and potassium at the exchangeable cationic sites, and a desorbent material compising para-diethylbenzene are used in combination in a process to separate para-xylene as an extract component from a feed mixture comprising para-xylene and at least one other $C_8$ aromatic isomer that both high para-xylene yields (greater than about 95%) and high para-xylene product purity (greater than about 99%) cannot be obtained simultaneously. The reason for this is because the particular adsorbent is more selective for para-diethylbenzene than it is for para-xylene. This relationship thus hinders the adsorption of para-xylene when the adsorbent contains desorbent material in the selective pore volume as it will after being contacted with desorbent material during the desorption step. Para-xylene entering the process with the feed input stream then does not easily and completely displace the para-diethylbenzene and itself become adsorbed in the following adsorption step. As a result a portion of the para-xylene is not adsorbed and is lost to the raffinate output stream thus reducing the yield of high-purity para-xylene product. Through manipulation of process operating conditions the product yield can be improved but at the expense of para-xylene purity. The result is that high product purity and yield cannot be obtained at the same time. I have found that an adsorbent comprising type X or type Y zeolite containing barium and strontium at the exchangeable cationic sites does not exhibit a higher selectivity for para-diethylbenzene than it does for para-xylene. When this adsorbent is employed in a para-xylene separation process along with a desorbent material containing para-diethylbenzene high para-xylene purity and yields can be obtained at the same time.

The following example is presented to illustrate the selectivity relationship that makes the improved process of my invention possible and is not intended to unduly restrict the scope and spirit of the claims attached hereto.

EXAMPLE

This example presents pulse test results for five adsorbents, A, B, C, D, and E. Adsorbents A and B comprise type X zeolite containing both barium and potassium at the exchangeable cationic sites; adsorbents C, D and E comprise type X zeolite containing barium and strontium at the exchangeable cationic sites. All adsorbents were prepared by ion exchanging Linde 13X Molecular Sieves as a base material, had a particle size range of approximately 20–40 U.S. Mesh and had a water content of about 4 wt. % measured by loss on ignition at 500° C.

The pulse test and test apparatus have been previously described. The feed mixture employed for each test contained 5 vol. % each of para-xylene, meta-xylene, ortho-xylene, ethylbenzene and n-nonane (used as a tracer) and 75 vol. % desorbent. The desorbent material was 30 vol. % para-diethylbenzene in normal heptane. The testing apparatus was maintained at a controlled temperature of 175° C. with sufficient pressure on the entire testing unit to maintain essentially liquid phase operations. From information derived from the chromatographic traces para-xylene (P) selectivities with respect to ethylbenzene (E), meta-xylene (M), orthoxylene (O) and para-diethylbenzene (p-DEB) were calculated as was the para-xylene retention volume. These selectivities and retention volumes are shown in Table No. 4 below.

it is for para-xylene. For adsorbents C, D and E, which have barium and strontium at the exchangeable cationic sites, the P/p-DEB selectivities are all greter than one indicating that the adsorbents are more selective for para-xylene than for para-diethylbenzene. Comparing the results for adsorbents C, D and E, it can be seen that as the weight ratios of barium to strontium for the adsorbents decrease from 13.2 for adsorbent C to 6.25 for adsorbent D to 2.92 for adsorbent E the P/p-DEB selectivities increase from 1.17 to 1.24 to 1.45 for adsorbents C, D, and E respectively. The improvement in P/p-DEB selectivities is also manifested by the increase in para-xylene retention volumes. At the same time, however, the para-xylene selectivities with respect to the other $C_8$ aromatic isomers generally decrease, particularly the P/M and P/O selectivities. For adsorbent C with a Ba/Sr weight ratio of 13.2 the P/O selectivity is over 3 but for adsorbent E with a Ba/Sr weight ratio of 2.92 the P/O selectivity has declined to a value less than 2. I have found that while adsorbents comprising type X or type Y zeolites containing barium and strontium at the exchangeable cationic sites in a barium to strontium weight ratio of from about 1:1 to about 15:1 or higher can be used in this process, the best balance of P/p-DEB selectivity and para-xylene selectivities with respect to the other $C_8$ aromatic isomers appears to be for those adsorbents having weight ratios of barium to strontium of from about 5:1 to about 15:1.

I claim as my invention:

1. A process for separating para-xylene from a feed stream comprising para-xylene and at least one other $C_8$ aromatic isomer which process comprises the steps of:
   a. contacting said feed stream at adsorption conditions with an adsorbent comprising type X or type Y zeolite containing barium and strontium in a weight ratio of barium to strontium of from about 1:1 to about 15:1 at the exchangeable cationic sites to effect the selective adsorption of para-xylene;
   b. removing a raffinate component comprising a less selectively adsorbed $C_8$ aromatic from said adsorbent;
   c. contacting said adsorbent with a desorbent material comprising para-diethylbenzene at desorption conditions to effect the desorption of para-xylene from said adsorbent; and, Table 4

| Adsorbent | Para-Xylene Selectivities | | | | |
| | A | B | C | D | E |
| --- | --- | --- | --- | --- | --- |
| Selectivities | | | | | |
| P/E | 1.61 | 1.62 | 1.70 | 1.67 | 1.65 |
| P/M | 3.72 | 3.96 | 3.86 | 3.16 | 2.56 |
| P/O | 3.35 | 3.57 | 3.12 | 2.67 | 1.98 |
| P/p-DEB | 0.675 | 0.901 | 1.17 | 1.24 | 1.45 |
| Wt. % SrO | — | — | 2.18 | 4.12 | 7.35 |
| Wt. % BaO | 21.0 | 26.0 | 27.3 | 24.5 | 20.4 |
| Wt. % $K_2O$ | 5.0 | 2.5 | — | — | — |
| Wt. Ratio Ba/Sr | — | — | 13.2 | 6.25 | 2.92 |
| P Retention Vol., cc | 17.1 | 19.3 | 27.5 | 29.0 | 33.0 |

The data first of all indicates that all the adsorbents are more selective for para-xylene than for ethylbenzene, meta-xylene or ortho-xylene since the P/E, P/M, and P/O selectivities are all greater than one. For adsorbents A and B, which have barium and potassium at the exchangeable cation sites, the P/p-DEB selectivities however are less than one indicating that the adsorbents are more selective for para-diethylbenzene than d. removing from said adsorbent an extract component comprising para-xylene.

2. The process of claim 1 further characterized in that said feed stream contains $C_8$ non-aromatics.

3. The process of claim 1 further characterized in that said feed stream contains ethylbenzene.

4. The process of claim 1 further characterized in that said feed stream contains ortho-xylene.

5. The process of claim 1 further characterized in that said feed stream contains meta-xylene.

6. The process of claim 1 further characterized in that said feed stream contains meta-xylene, ortho-xylene and ethylbenzene.

7. The process of claim 1 further characterized in that said adsorbent comprises type X zeolite.

8. The process of claim 1 further characterized in that said adsorbent contains a weight ratio of barium to strontium of from about 5:1 to about 15:1.

9. The process of claim 1 further characterized in that said adsorption conditions and desorption conditions include a temperature within the range of from about 20° to about 230° C. and a pressure within the range of from about atmospheric to about 500 psig. to insure liquid phase.

10. A process for the separation of para-xylene from a feed stream comprising para-xylene and at least one other $C_8$ aromatic isomer which process employs an adsorbent comprising type X or type Y zeolite containing barium and strontium in a weight ratio of barium to strontium of from 1:1 to about 15:1 at the exchangeable cation sites and which process comprises the steps of:
 a. maintaining net fluid flow through a column of said adsorbent in a single direction, which column contains at least three zones having separate operational functions occurring therein and being serially interconnected with the terminal zones of said column connected to provide a continuous connection of said zones;
 b. maintaining an adsorption zone in said column, said zone defined by the adsorbent located between a feed input stream at an upstream boundary of said zone and a raffinate output stream at a downstream boundary of said zone;
 c. maintaining a purification zone immediately upstream from said adsorption zone, said purification zone defined by the adsorbent located between an extract output stream at an upstream boundary of said purification zone and said feed input stream at a downstream boundary of said purification zone;
 d. maintaining a desorption zone immediately upstream from said purification zone, said desorption zone defined by the adsorbent located between a desorbent input stream at an upstream boundary of said zone and said extract output stream at a downstream boundary of said zone;
 e. passing said feed stream into said adsorption zone at adsorption conditions to effect the selective adsorption of para-xylene by said adsorbent in said adsorption zone and withdrawing a raffinate output stream from said adsorption zone;
 f. passing a desorbent material comprising para-diethylbenzene into said desorption zone at desorption conditions to effect the displacement of para-xylene from the adsorbent in said desorption zone;
 g. withdrawing an extract stream comprising para-xylene and desorbent material from said desorption zone;
 h. passing at least a portion of said extract output stream to a separation means and therein separating at separation conditions para-xylene from said desorbent material to produce a para-xylene product substantially free of desorbent material; and,
 i. periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

11. The process of claims 10 further characterized in that said feed stream contains $C_8$ non-aromatics.

12. The process of claim 10 further characterized in that said feed stream contains ethylbenzene.

13. The process of claim 10 further characterized in that said feed stream contains ortho-xylene.

14. The process of claim 10 further characterized in that said feed stream contains meta-xylene.

15. The process of claim 10 further characterized in that said feed stream contains meta-xylene, ortho-xylene and ethylbenzene.

16. The process of claim 10 further characterized in that said zeolite comprises type X zeolite.

17. The process of claim 10 further chharacterized in that said adsorbent contains a weight ratio of barium to strontium of from about 5:1 to about 15:1.

18. The process of claim 10 further characterized in that it includes the step of passing at least a portion of said raffinate output stream to a separation means and therein separating at separation conditions raffinate components from desorbent material to produce a raffinate product substantially free of desorbent material.

19. The process of claim 10 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

20. The process of claim 10 further characterized in that said adsorption conditions and desorption conditions include a temperature within the range of from about 20° to about 230° C. and a pressure within the range of from about atmospheric to about 500 psig to insure liquid phase.

* * * * *